(12) United States Patent (10) Patent No.: US 9,370,237 B2
Hiemenz et al. (45) Date of Patent: Jun. 21, 2016

(54) ACTIVE SPINAL SUPPORT SYSTEM

(71) Applicants: Gregory J. Hiemenz, Silver Spring, MD (US); Curt S. Kothera, Crofton, MD (US); Pablo J. Sztein, College Park, MD (US)

(72) Inventors: Gregory J. Hiemenz, Silver Spring, MD (US); Curt S. Kothera, Crofton, MD (US); Pablo J. Sztein, College Park, MD (US)

(73) Assignee: Innovital LLC, Calverton, MD (US)

( * ) Notice: Subject to any disclaimer, the term of this patent is extended or adjusted under 35 U.S.C. 154(b) by 192 days.

(21) Appl. No.: 14/181,148

(22) Filed: Feb. 14, 2014

(65) Prior Publication Data

US 2014/0224849 A1   Aug. 14, 2014

Related U.S. Application Data

(60) Provisional application No. 61/764,313, filed on Feb. 13, 2013.

(51) Int. Cl.
*A45F 3/04* (2006.01)
*A45F 3/06* (2006.01)
*A45F 3/08* (2006.01)
*A42B 3/04* (2006.01)
*A41D 13/05* (2006.01)
*A61F 5/02* (2006.01)
*A45F 3/14* (2006.01)

(52) U.S. Cl.
CPC .............. *A45F 3/04* (2013.01); *A41D 13/0531* (2013.01); *A42B 3/0473* (2013.01); *A45F 3/06* (2013.01); *A45F 3/08* (2013.01); *A61F 5/026* (2013.01); *A45F 2003/045* (2013.01); *A45F 2003/144* (2013.01)

(58) Field of Classification Search
CPC ..... A41D 13/0531; A61F 5/024; A61F 5/026; A45F 3/04; A45F 3/06; A45F 3/08; A45F 2003/045; A45F 2003/144; A42B 3/0473; A47C 7/40; A47C 7/425; A47C 7/46; A47C 7/462
USPC ..................... 224/261, 262; 602/19
See application file for complete search history.

(56) References Cited

U.S. PATENT DOCUMENTS

| | | | | |
|---|---|---|---|---|
| 3,945,376 A * | 3/1976 | Kuehnegger | ............ | A61F 5/026 602/19 |
| 4,911,346 A * | 3/1990 | Shallman | .................. | A45F 3/08 224/153 |
| 4,923,147 A * | 5/1990 | Adams | ................. | A42B 3/0473 244/122 AG |
| 5,498,233 A * | 3/1996 | Stojanovic | ......... | A41D 13/0512 128/845 |
| 7,270,377 B2 * | 9/2007 | Schmitz | ................. | A47C 7/425 297/230.1 |
| 7,822,522 B2 | 10/2010 | Wereley | | |
| 2003/0050581 A1* | 3/2003 | Berns | ................. | A41D 13/0531 602/3 |

(Continued)

*Primary Examiner* — Corey Skurdal
(74) *Attorney, Agent, or Firm* — Ober, Kaler, Grimes & Shriver; Royal W. Craig (57) ABSTRACT

A wearable spinal support system having an upper body adapter engaging the head and/or torso of a wearer and a lower body adapter engaging the hips/pelvis, the upper and lower body adapters joined by an articulated structural column. The structural column is made up of stacked vertebral elements each having an aperture provided there through such that a tendon can be fed through the aligned apertures of the vertebral elements. The tendons are fixed at one end and each engaged to mechanical control element at the other end such that the tension/payout in each tendon is independently variable under direction of a controller receiving sensor feedback in order to support the loaded upper body of the wearer and position it relative to the lower body when desirable according to the controller.

27 Claims, 6 Drawing Sheets

(56) References Cited

U.S. PATENT DOCUMENTS

| | | | | |
|---|---|---|---|---|
| 2005/0015859 A1* | 1/2005 | Ashline | ............... | A42B 3/0473 2/421 |
| 2007/0156074 A1* | 7/2007 | Cojbasic | ................. | A61F 5/026 602/19 |
| 2010/0263111 A1* | 10/2010 | Leatt | .................. | A41D 13/0512 2/467 |
| 2010/0268137 A1* | 10/2010 | Bachmann | ............ | A61F 5/0102 602/16 |
| 2011/0105971 A1* | 5/2011 | Ingimundarson | ....... | A61F 5/024 602/19 |
| 2012/0131736 A1* | 5/2012 | Reimer | .............. | A41D 13/0531 2/467 |
| 2013/0009445 A1* | 1/2013 | Cooper | ................... | A61F 5/026 297/468 |
| 2014/0039371 A1* | 2/2014 | Johnson | .................... | A61F 5/02 602/19 |
| 2014/0245529 A1* | 9/2014 | Beckman | ........... | A41D 13/0531 2/468 |
| 2014/0378882 A1* | 12/2014 | Kazerooni | ................ | A61F 5/01 602/19 |

* cited by examiner

Front View
Fig. 1

ACTIVE SPINAL SUPPORT SYSTEM

CROSS-REFERENCE TO RELATED APPLICATION(S)

The present application derives priority from U.S. Provisional Application Ser. No. 61/764,313 filed 13 Feb. 2013.

BACKGROUND OF THE INVENTION

1. Field of the Invention

The present invention relates generally to support systems for clothing and body worn equipment, and more particularly, to active support systems for clothing, equipment and/or other body worn items including jackets, backpacks, football helmets/pads, and other military and non-military clothing and gear. The invention actively off-loads bodyworn item loads to reduce back fatigue, and also during a seated shock event for enhanced protection of the wearer.

2. Description of Prior Art

Occupant survivability is a top priority for the design of military ground vehicles as more than 4,400 casualties in recent conflicts, or over 60% of the total casualties, have been the result of the effects of Improvised Explosive Devices (IEDs) on ground vehicles. Operational demand for ground vehicles in areas with high potential for IEDs has increased, and this accentuates the need for enhanced war-fighter protection to vehicular underbody blast events. In addition to the extreme forces resulting from explosive devices, it has been shown that shock and vibration resulting from normal vehicular operations leads to fatigue, back pain, and long-term chronic injuries which result in premature departure of highly trained individuals. Energy absorbing (EA) systems are used within the seat mountings of vehicles to attenuate the loads transmitted to the occupants. These offer protection to soldiers in case of extreme IED events. One such system is an adaptive seating suspension utilizing an actively controlled magnetorheological (MR) fluid based dampener to provide optimized occupant protection to extreme shock events and also to provide vibration control during normal vehicle operation. As described more fully in U.S. Pat. No. 7,822,522 which is incorporated herein by reference, these systems automatically adapt to occupant weight and environmental conditions (e.g. blast severity and vibration profiles) and have been proven to provide optimized protection while minimizing required seat stroke.

The amount of equipment that soldiers and aviators are required to bear upon their upper torso contributes to the problem. The average weight of such equipment has increased from 5-6 lbs in the 1970s-1980s to upwards of 80-100 lbs today. This can more than double the total mass supported by an individual's spine, which significantly increases the chances of acute injuries (during extreme events) as well as long-term chronic injuries from normal operations. For example, 80 lbs of additional lumbar-supported equipment weight for a soldier experiencing a 20 G pelvic acceleration increases the lumbar compression load by 1600 lbs which roughly doubles the expected lumbar load as compared to the same event without the additional equipment. Such a load is above the allowable tolerance for spinal injury under some metrics. One widely utilized performance metric for blast survivability is the Dynamic Response Index (DRI) which was developed in the late 1960's and 1970's for ejection seats and which utilizes a second order differential equation with assumed biodynamic properties (mass, stiffness, damping) to estimate the likelihood of spinal damage. However, this metric utilizes only a pelvis or seat pan acceleration profile for input and assumes a $50^{th}$ percentile aviator with minimal lumbar-supported equipment. As a result, an acceleration profile which passes DRI may be entirely insufficient to protect a modern, gear laden vehicle occupant. The same is true for other acceleration-based injury metrics (7 millisecond clip, Eiband, etc.) because the tolerable levels were identified with much lower lumbar-supported mass levels.

Studies are underway to update and develop new injury tolerance metrics based either on spinal (lumbar) load or, if acceleration based, will at least take into account the additional equipment masses that the modern warfighter is expected to wear. These new/updated metrics will have an alarming effect on the perceived performance of currently fielded seating solutions because they will show that many such systems provide inadequate protection.

More recent studies by experts in vehicular occupant safety have shown that seat based attenuation systems would require an increased seat stroke of 60-80% to maintain lumbar loads within current tolerance levels with a mass of lumbar-supported equipment of about 45 lbs. This is difficult if not impossible since seat stroking distance is already limited and overmatched by blast forces.

One solution to the problem of increased lumbar-supported weight is simply to off-load the spine but this is not practical from an operation perspective because much of this equipment is mission and/or safety critical. Methods of alternatively supporting the additional equipment/mass by other structure such as the vehicular seat are possible but suffer from concerns of limited mobility and hindered vehicular egress. What is needed is an independent or integrated lumbar support system able to supplement the human body's ability to support weight on the upper torso. Such a system would need to be lightweight, unobtrusive so as not to hinder movement, independently powered (or passive, i.e., unpowered), and capable of quickly adapting to a variety of environmental variables to protect the spine of the wearer in a range of high shock or repetitive shock events.

SUMMARY OF THE INVENTION

The present invention is a wearable spinal support system providing a secondary "backbone" to transmit the additional gear loading to the lower torso (sub lumbar) and/or directly to the seat structure. The system has an upper body adapter engaging the torso of a wearer and a lower body adapter engaging the waist, the upper and lower body adapters joined by an articulated structural column. The structural column is made up of stacked, vertebral elements through each of which an aperture is provided such that a tendon can be fed through the aligned apertures of each arm and the stem. The tendons are fixed at one end and each engaged to a mechanical control element (e.g., an actuator or spring) at the other such that the tension/payout in each tendon is independently variable or managed under direction of a controller receiving sensor feedback in order to support the loaded upper body of the wearer and position it relative to the lower body when desirable according to the controller. The actuators may be electromechanical motors, pneumatically actuated muscles, or other mechanical actuation devices. The present system will automatically adjust the provided support to allow freedom of movement while off-loading the wearer's back through a full spectrum of operational scenarios and motions thereby reducing back fatigue and risk of long-term chronic injuries resulting from dismounted operations or from exposure to shock and vibration while in transit. Additionally, when experiencing a high shock event in a tactical vehicle, such as an underbody blast event, the system actuates to optimally position the body and redirect added equipment mass into the vehicle seat structure and ensure safe spinal loading with no penalty on seat stroking distance.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

Disclosed is a human-wearable, spinal support system 1 integrable into any body worn equipment, clothing, gear or load carrying systems for military and non-military applications, including backpacks/rucksacks, jackets, football helmets/pads, body armor, and other clothing and/or gear (collectively "body worn items") that may also be actively actuated. The system generally incorporates upper and lower body engaging elements joined by the structural backbone element which includes at least one external interoperability fixture for cooperative engagement with a vehicular structure such as a seat or frame bearing point. Under the control of a digital control system which receives information from one or more sensors (e.g., position, tension, acceleration, etc.), an actuated tensioning system adjusts to allow freedom of movement of the wearer while reducing the load of the supported equipment transmitted to the wearer's musculoskeletal system. Then, upon onset of a shock event, the tensioning system influences the body position of the wearer in order to minimize the forces experienced and divert the applied forces when possible to surrounding structures. Under normal operating conditions the system provides support to the wearer's body to counter the fatiguing effect of vibration and chronic injury resulting from long term exposure.

Figure 1:
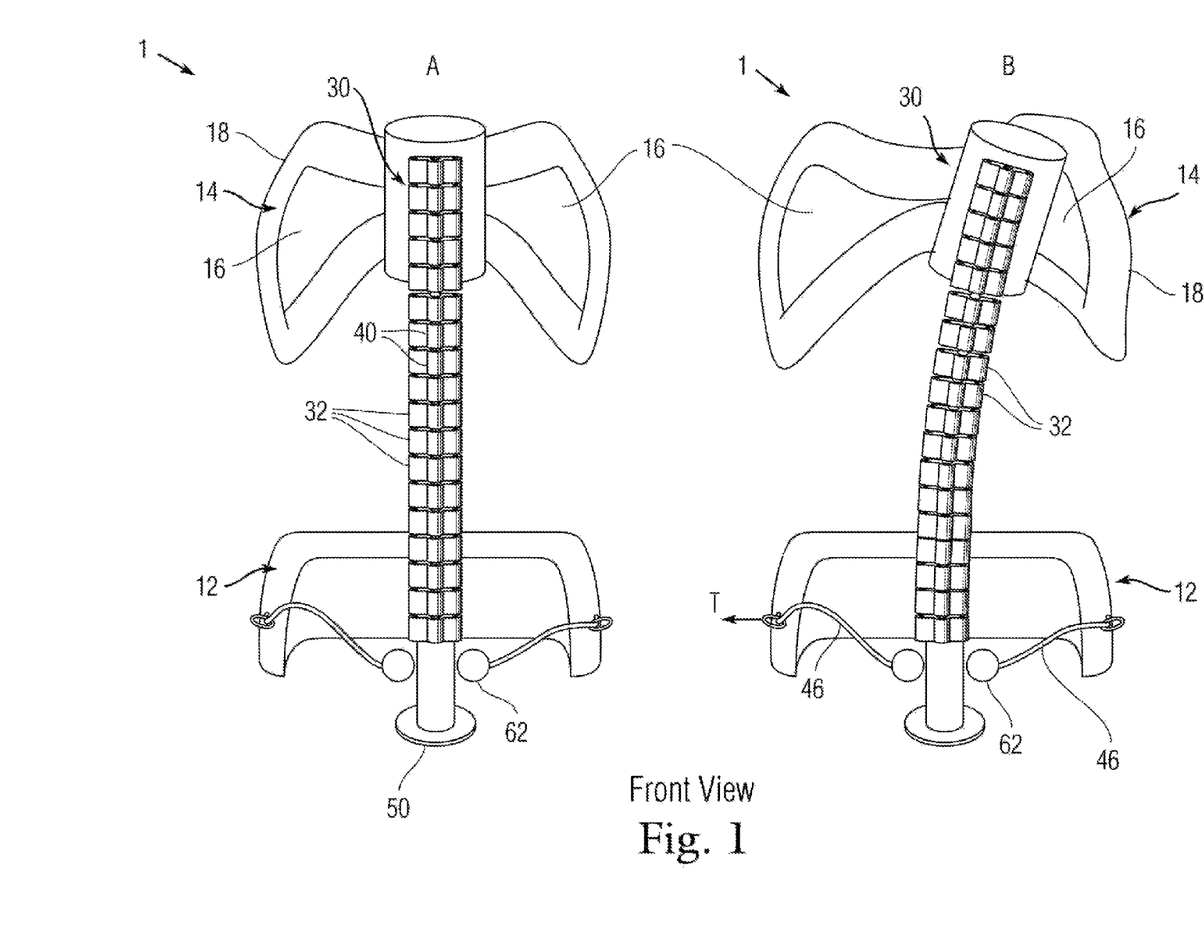
FIG. 1 is a front schematic view of an active spinal support system according to the present invention in an upright, neutral position (A) and flexed position (B).
Figure 2:
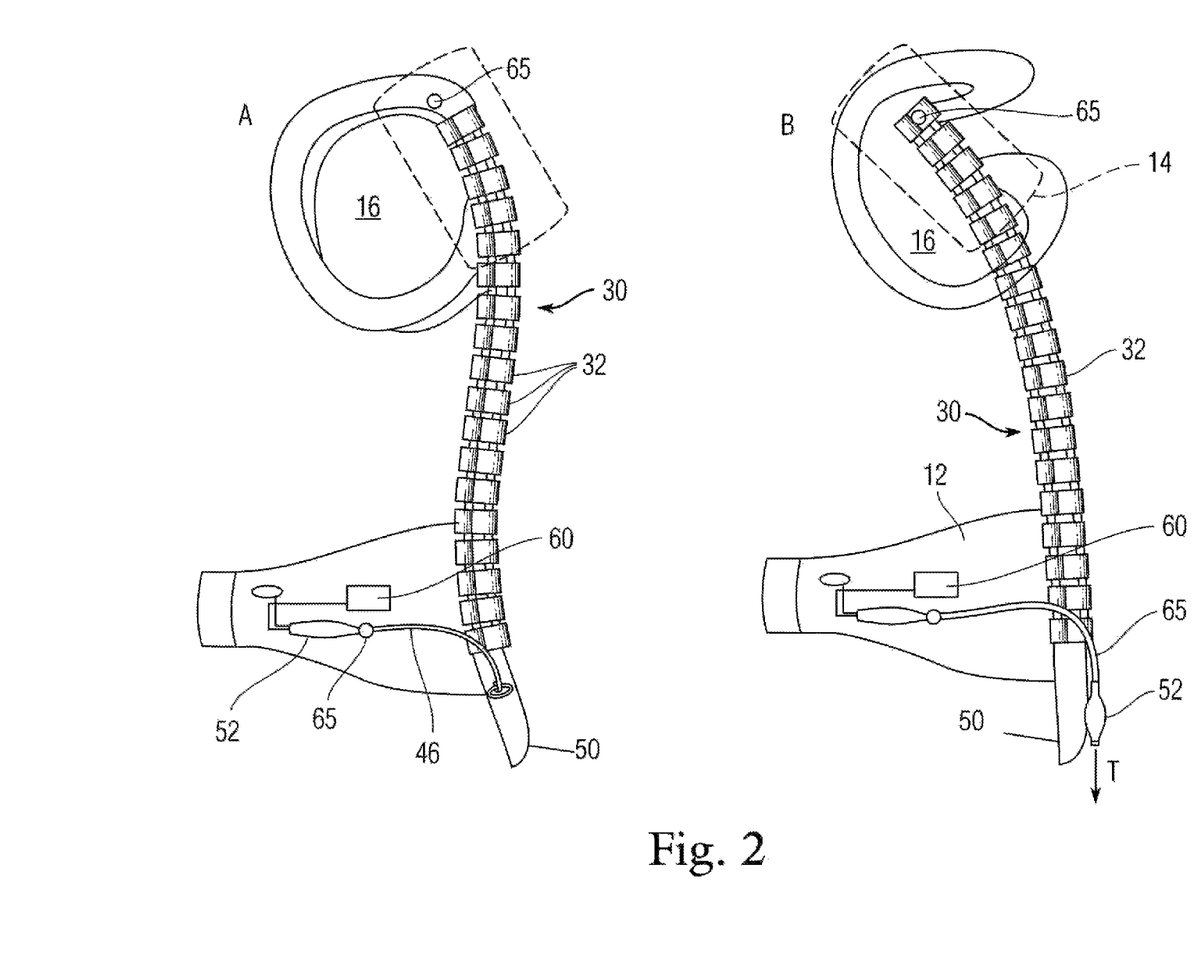
FIG. 2 is a side schematic view of an active spinal support, system according to the present invention in a neutral position (A) and in neutral flexed position (B).
Figure 3:
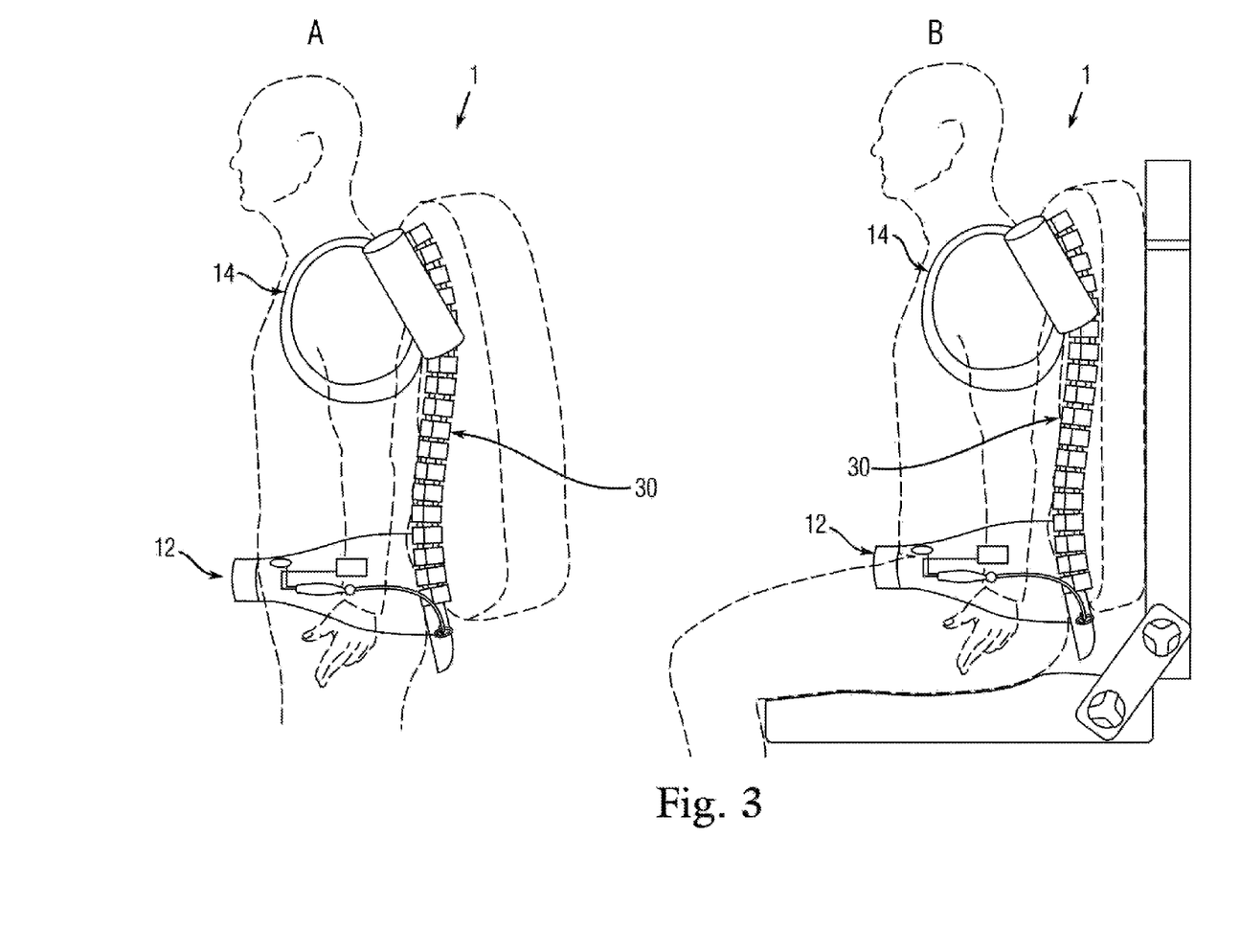
FIG. 3 is a side schematic view of an active spinal support system according to the present invention worn by a wearer in a standing position (A) and in a seated position (B).

With reference to FIGS. 1 and 2, an embodiment according to the present invention is depicted including a lower body adapter 12 and an upper body adapter 14. The lower body adapter is preferably a belt of adjustable length extendable around the waist of the wearer in the nature of the waist belt of the U.S. Army's Modular Lightweight Load-carrying Equipment (MOLLE) pack system. The lower body adapter 12 is preferably constructed of a strong, lightweight material such as woven or non-woven natural or synthetic fabric and includes padded portions for secure engagement with the waist/hips of the wearer when adjusted to a correct length. In an alternate embodiment the lower body adapter 12 may take the form of a pant such as a compression pant preferably (but not necessarily) including at least some padding or construction so as to securely engage the hips of the wearer at the waist.

The upper body adapter 14 preferably comprises a shoulder harness extending across at least the upper back of the wearer and including straps 18 defining arm holes 16 for receiving the arms of the wearer and securely engaging his or her upper body, though embodiments also exist where armholes 16 are not clearly defined as is the case when the straps 18 have structural stiffness of their own and do not loop back around (e.g., like a harness). The straps 18 may be constructed of nylon or other webbing and extend over the shoulder of the wearer before looping back under the arm of the wearer to form the arm holes 16 as depicted. In another embodiment the upper body adapter 14 may be a preformed unit in the nature of a vest in which armholes 16 are provided. The upper body adapter 14 is sized (adjustably or fixed) to securely engage the upper torso above the abdominal region and may be sewn, molded or otherwise constructed of a woven or non-woven polymer or synthetic fabric preferably having sufficient elasticity to securely engage the body without overly limiting movement on the part of the wearer. The upper body adapter 14 may be adapted to be worn over or as an article of clothing or may be integrated onto an existing Molle harness or other load bearing harness system. Alternately the upper body adapter 14 may be integrated into an element of a body armor system such as the Outer Tactical Vest (OTV) of the Interceptor body armor fielded by the U.S. Army. The upper body adapter is preferably designed such that it does not transmit/react vertical loads to the wearer's upper torso and, rather, only transmits/reacts lateral loads.

The upper body adapter 14 and lower body adapter 12 are joined by a structural vertebral system ("SVS") 30. The SVS 30 comprises an elongate artificial spine constructed of a series of stacked vertebral elements 32 linked together in series. With additional reference to FIG. 4, the vertebral elements 32 preferably have a T-shaped cross-section and are oriented such that the flat "top" surface formed by the arms 34 of the "T" faces forward and the stem 36 of the "T" faces rearward. The vertebral elements 32 are preferably constructed of a strong yet lightweight polymer such as polyoxymethylene (a.k.a. acetal resin and sold under the brand names such as Delrin® and Celcon) but may also be made of metals such as aluminum alloy or a combination of polymers and metallics. The preferred T-shape described herein is not intended to be limiting, however. One having ordinary skill in the art would understand that one of among many other structural configurations could be adopted without deviating from the invention, such as vertebral elements having cross-sections of rectangular, circular, triangular, etc. form, or vertebral elements of predominantly solid or predominantly tubular form. As such the vertebral element 32 could be a predominantly solid T-shaped element, as depicted in FIG. 4, or it could likewise be of rectangular tube construction while still serving the intended function.

In order to transmit axial loading while allowing relative rotational movement between the stacked vertebral elements 32, an intervertebral spacer 40 is provided between each of the vertebral elements and is preferably disc or spherically shaped. In this way, an intervertebral spacer 40 acts as a hinge between two stacked vertebral elements 32, albeit a multidirection hinge. An indentation 38 is provided at the intersection of the stem 36 and arms 34 on the upper 15 and lower 17 surfaces of the vertebral elements 32 to seat the spacer 40. The spacers 40 are seated in the indentations 38 which are cooperatively formed. This configuration allows movement of the SVS 30 in concert with the movement of the wearer. Alternately, the intervertebral spacers 40 may be formed as ellipsoidal (oblate or prolate) or other suitable shapes so as to favor certain motions over others as in the pictured preferred embodiment, or likewise, the intervertebral bodies 40 may be formed from a conventional hinge, which allows relative rotational movement about only one axis. The intervertebral spacer 40 is likewise made of a hard, strong and lightweight material with high abrasion resistance. One or more protrusions (not shown) on the upper and/or lower surfaces 15, 17 of the vertebral elements 32 may be provided between some or all of the vertebral elements 32 to limit, bias or otherwise control the relative motion and orientation of adjacent elements. For example, a protrusion on the upper surface 17 of a vertebral element 32 at or near the distal end of the stem 36 would limit extension of the SVS 30 and thus extension of the spine of the wearer. The position and dimensions of the protrusion(s) will determine the limit of such motion. This limited motion could also be considered as an auxiliary stable position for the SVS 30. Furthering this notion of additional stable positions, the vertebral elements 32 may also contain features such as angled flat surfaces that provide sufficient bearing surface for the SVS 30 to be stable in at least one other position, which may include a flexed position that is commonly encountered by the wearer.

Figure 4:
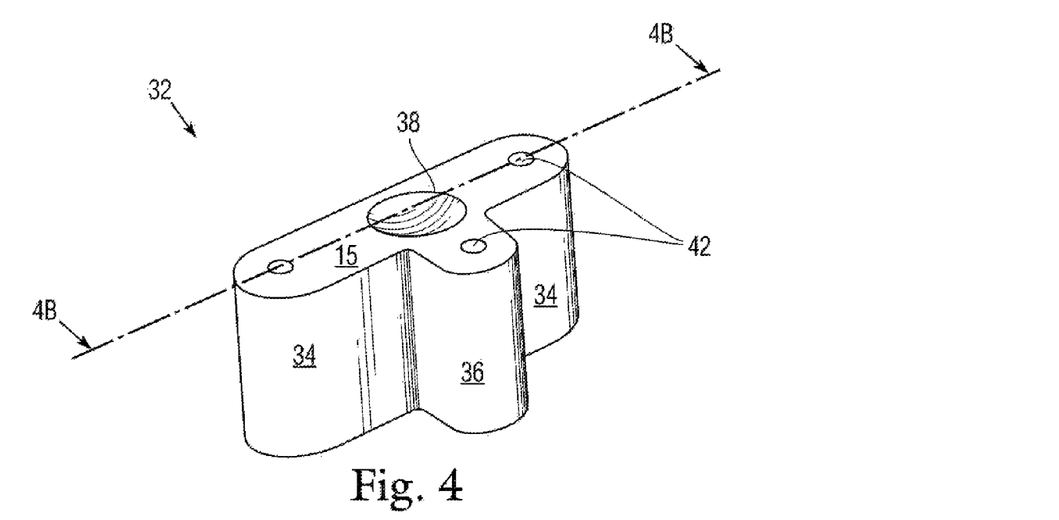
FIG. 4 is a perspective view of an exemplary vertebral element 32 according to the present invention.
Figure 5:
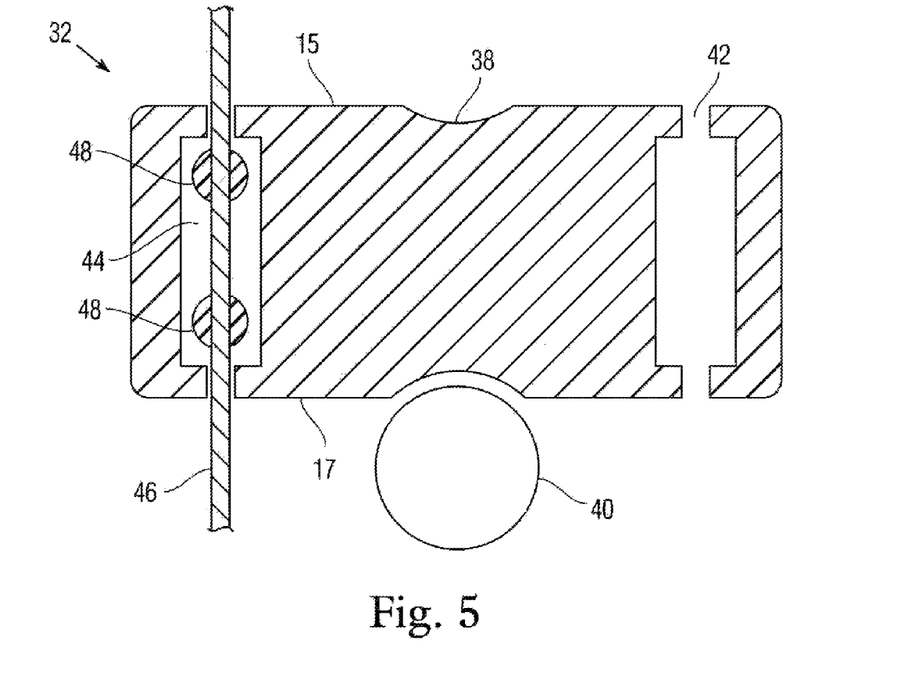
FIG. 5 is a side cross-section of an exemplary vertebral element 32 as in FIG. 4.

With reference to FIGS. 4 and 5, each arm 34 and the stem 36 are provided with a substantially vertical hole 42 extending longitudinally (with, respect to the linear member) from the upper surface 15 to the lower surface 17. In certain embodiments the diameter of the hole 42 is constant. In another embodiment the diameter of the hole is enlarged within the vertebral element 32 to form a cavity 44 along the length of the hole 42. With reference to FIGS. 1 and 2, a tendon 46 is provided through each of the cooperatively aligned holes 42 in the arms and stem, of the vertebral elements 32. The tendon 46 may be fixed to each vertebral element 32 or may, at select locations along the length of the linear member, be permitted limited sliding movement within the holes 42 before engaging the vertebral element to control the overall shape, applied force and movement of the SVS 30. In the depicted embodiment, limited sliding movement of the tendon within the holes 42 is accomplished by affixing one or more stops 48 on the tendon 46 within the cavity 44 as shown in FIG. 5. In certain embodiments it may be desirable to permit sliding of the tendon through the holes 42 of one or more vertebral elements without restriction.

With reference to FIGS. 1 and 2, each tendon 46 terminates at the topmost vertebral element 32 in the stack which is affixed to the upper body adapter 14. The bottom most vertebral element 32 is affixed to the lower body adapter 12 such that the SVS 30 is positioned substantially parallel to the spine within the sagittal plane. A seat support fixture 50 is preferably rigidly affixed to or integrally formed with the bottom most vertebral element 32 and extends downward for cooperative engagement with a vehicle seat or other support structure as will be described. Tendon 46 may preferably be constructed of a polymer or metallic wire or multistrand cable having high strength and high Young's modulus (low stretch). In another preferred embodiment, tendon 46 forms an elongate spring. In yet another embodiment, the preferred plurality of tendons 46 may be replaced with at least one strap or webbing (e.g., similar to an automotive seatbelt). In this latter embodiment, the longitudinal holes 42 may more precisely be described as longitudinal slots. In all such embodiments, the longitudinal holes 42 are not meant to limit the invention. For example, the tendon 46 may likewise couple (e.g., guide, align) the vertebral elements 32 from an external position.

As seen in FIG. 2, the lower end of each tendon 46 is affixed to a mechanical control element 52, such as an actuator. More specifically, in a preferred embodiment the lower end of each of the tendons 46 that run through the left and right arms 34 of the vertebral element 32 is routed into the lower body adapter 12 which houses the mechanical control element 52. The mechanical control element 52 is affixed within the lower body adapter 12 and is engaged to the tendon 46 so as to be able to pull-on or tension the cable as is determined to be desirable by an onboard controller 60 when mechanical control element 52 is an active component (e.g., actuator). Also as shown in FIG. 1, a pulley element or turning button 62 of low friction and high abrasion resistance may be affixed to or within the lower body adapter 12 to facilitate routing of the tendon 46 from the lower body adapter 12 to the SVS 30. One skilled in the art will understand that mechanical control element 52 may include some lever, gearing or other kinematic mechanism not pictured to provide mechanical advantage or other tailoring of the force-stroke characteristics of the mechanical control element 52. The lower end of the tendon 46 that is fed through the stem 36 of the vertebral elements 32 is similarly engaged to mechanical control element 52 affixed to the bottom most vertebral element 32 (FIG. 2) or to the seat support fixture 50 (FIG. 2) The tension in each tendon 46 may be selectively varied by the onboard mechanical control elements 52 as will be described so as to alter the shape of the SVS 30 to support the load borne by the upper body of the wearer and even the upper body itself, while also allowing freedom of motion. The tendon tension may further be varied when desirable to influence (i.e. move) the position of the upper body adapter 14 (and thus the upper body of the wearer) relative to the lower body adapter 12 at the hips of the wearer.

Mechanical control elements 52, when active, may be any electromechanical actuator (e.g., DC or stepper motors), or hydraulic actuators, pneumatic, electric or mechanical actuators. Mechanical control elements 52, when passive, may be any components such as springs (linear, nonlinear, or constant force), dampers, or levers, with or without a corresponding controller 60. In a preferred embodiment, mechanical control elements 52 are Pneumatic Artificial Muscles (PAMs).

Figure 6:
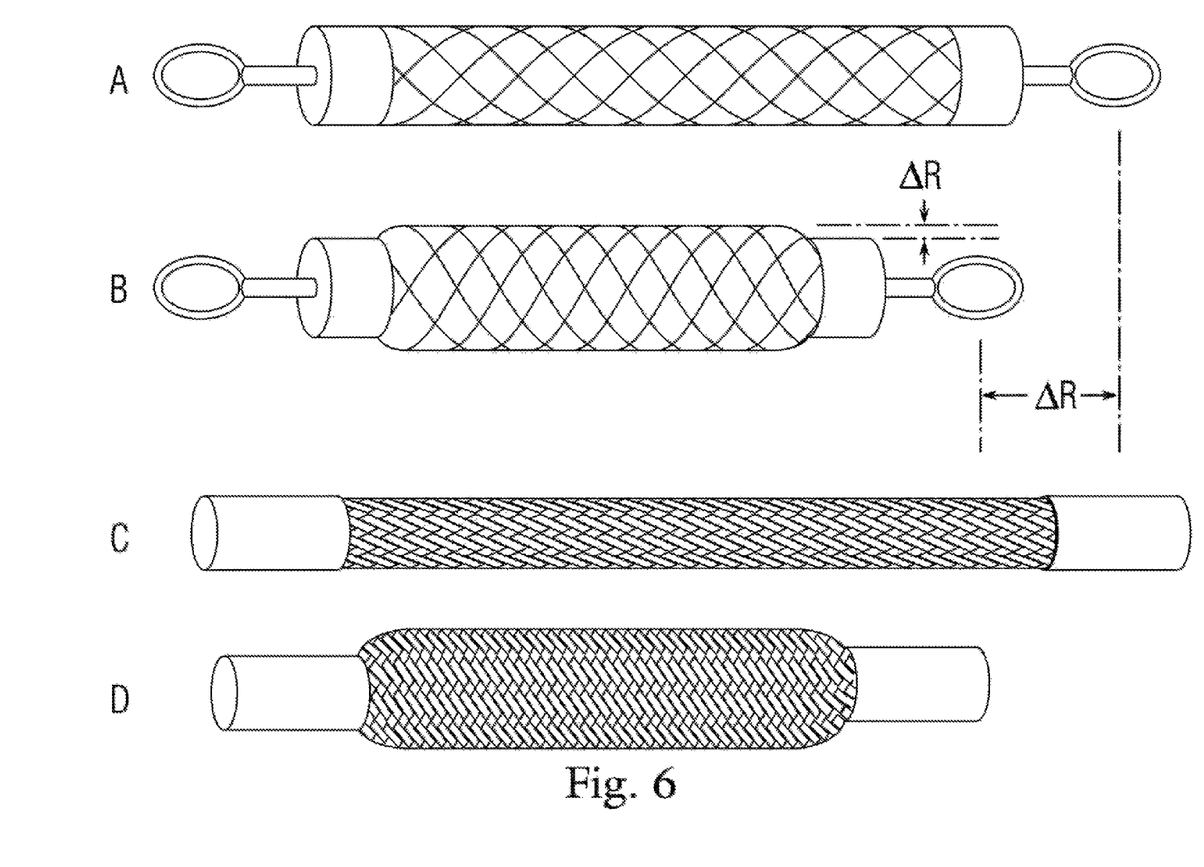
FIG. 6 is a composite illustration of a schematic view of an exemplary Pneumatic Artificial Muscle (PAM) actuators both unpressurized (A,C) and pressurized (B,D) as utilized in an embodiment of an actuated active spinal support system according to the present invention.

With reference to FIG. 6, PAMs are similar to natural muscles in that a pulling force is generated upon activation. They consist of an elastomeric bladder (most commonly natural rubber) encased by a double helical wire braid (typically PET or Kevlar). As the bladder is pressurized with a fluid (gas) (FIG. 6(B,D)), it expands in the radial direction while contracting in the longitudinal direction. This radial expansion causes the angle of the braid fibers to increase, resulting in a net decrease in muscle length. The pulling force is generated during this geometrical change, and the geometrical re-orientation can produce significantly more force than similarly sized pneumatic/hydraulic cylinders at the same pressure. As an example of the large variation in performance that is possible with these actuators, a 2-in long, 0.125-in diameter PAM (3 grams) may have a blocked force of 18 lbs and free stroke of 0.23 inches at 90 psi, whereas a 12-in long, 2-in diameter PAM (950 grams) may have a blocked force over 4,000 lbs and free stroke over 3 inches at only 90 psi. As can be seen from these numbers, the force-to-weight ratios of these actuators can be on the order of 20,000 N/kg (2,000 lb/lb), making them ideal candidates for weight-critical devices such as the present invention. In addition to their high performance and light weight, PAMs also feature inherent compliance which gives them a more natural feel to human-actuator interaction systems such as the present invention. PAMs offer a very lightweight actuation system that can be powered by replaceable miniature compressed gas cartridges (e.g., air or $CO_2$), either disposable or refillable, but also require an electrical power source to actuate gas release valves for operation of the muscles. Electromechanical motors are a more conventional actuation technology and the basic characteristics of such systems are known to those skilled in the art such that a detailed description is not here required. It is, however, noted that electromechanical systems am entirely from an electrical power supply and so require only a single power source which eliminates the need for certain elements of an embodiment actuated purely by electromechanical means.

In addition to one or more mechanical control elements 52, when active, the lower body adapter 12 houses an onboard controller 60 preferably in the form of a self contained digital microprocessor and memory. The controller 60 receives input from one or more sensors 65 indicating certain parameters of the spinal support system 1 as well as additional environmental parameters. In a preferred embodiment, at least one sensor 65 is provided in communication with the controller to sense and report the force (tension) in each tendon 46. Sensors 65 may be, for example, encoder displacement sensors, force transducers, strain gauges, accelerometers, or the like, or any other type of sensor known to those skilled in the art and capable of providing feedback to controller 60 regarding the position of, or forces acting on, the wearer. Based on this information, the controller 60 employs an algorithm (e.g., tension feedback) to variously allow the tendons 46 to payout as required to accommodate forward and sideways bending of the wearer's back, while providing sufficient tension to provide support for the wearer's equipment load under normal operational conditions. Upon an extreme shock event in mounted operations, the controller may tension and retract the tendons 46 to ensure that the SVS 30 is straightened for supporting the resulting shock load and transmitting it away from the occupant's spine and into the seat structure. Additional sensors such as one or more position sensors (to determine/confirm the position of the SVS 30), and one or more accelerometers may be operatively connected to the controller 60 to provide additional information on which to determine optimum SVS 30 position and corresponding tensions of the tendons 46.

In another embodiment of the present invention, the SVS 30 is designed to off-load the applied forces of body-worn equipment weight, shock events, normal vehicular operation, and the like, directly to the vehicle's seat structure, bypassing the wearer's lower body altogether. In this embodiment the lower body adaptor 12 is eliminated, and SVS 30 and the lower end of tendons 46 are coupled to the vehicle seat via seat fixture 50. Where active control (e.g., tension) of SVS 30 is desirable, such control can be accomplished through a mechanical control element 52, controller 60, and sensors 65 mounted in upper body adaptor, 14, and providing the same functions as those devices described herein in relation to the lower body adaptor 12 from the opposite end of SVS 30. To accommodate this configuration, upper body adaptor 14 could be expanded to include, for example, a "backpack"-type carrier containing the mechanical control element 52 and controller 60 and attached to upper body adaptor 14 or straps 18, or by increasing the amount of material forming upper body adaptor 14 and integrating mechanical control element 52 and controller 60 directly therein. Additional material used to construct the additional aspects of upper body adaptor 14 needed to achieve this configuration may be the same materials as those described with respect to upper body adapter 14 above.

In yet another embodiment, mechanical control element 52 and controller 60 may be integrated into upper body adapter 14, and lower body adapter 12 functions solely to couple SVS 30 to the wearer's lower body and/or seat support 50 to enable SVS 30 to assist in actively positioning the wearer's body in response to a shock event or the like. In yet another embodiment the lower body adapter 12 performs this coupling function while also housing mechanical control element 52 and controller 60 as depicted in the first preferred embodiment, but without being mechanically engaged to SVS 30 such that all forces applied to the wearer's upper body are transferred directly to the seat structure through the seat support or the like, with which bottom vertebral element 32 may be integrally formed. According to this instant preferred embodiment, only tendons 46, but no weight-bearing aspects of SVS 30, are actively coupled to lower body adaptor 12.

In yet another embodiment mechanical control element 52 is a passive (i.e., not actively controllable) component such as a spring, negating the need of controller 60 and sensors 65. This embodiment maintains "control" of the spinal support system 1 through its chosen (i.e., prescribed) force-stroke/payout characteristics. Active control is not possible in this embodiment, but the ability to optimally off-load the wearer is exchanged for a system that requires no electrical, or other, power source, which may be preferred in certain applications (e.g., fail-safe design). As described above for the active variant of mechanical control element 52, the passive mechanical control element 52 may likewise include a kinematic mechanism to allow for mechanical advantage. Alternatively, a passive mechanical control element (e.g., spring) may be placed in parallel to an active mechanical control element 52 (e.g., actuator) to provide a means of fail-safety if, for example, electrical power was lost or otherwise exhausted.

Figure 7:
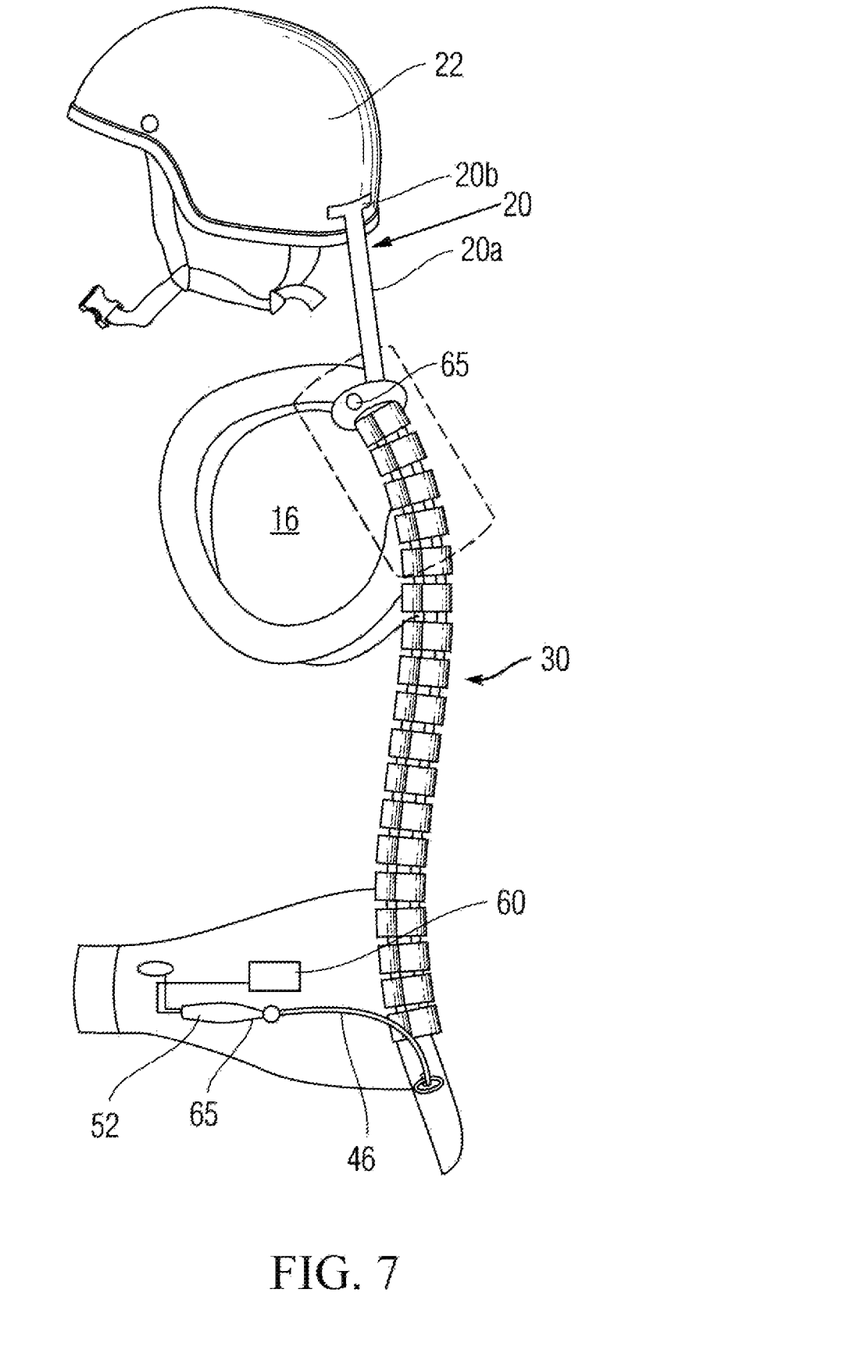
FIG. 7 is a composite view of an active spinal support system with a helmet support element 20 that mechanically engages with a helmet 22 also worn by the wearer.

In addition to the weight of packs or equipment worn by a soldier on his or her upper body, their helmets also place a considerable load on the soldier's spine. This is especially true where night vision goggles and/or other forms of eye protection are attached. Accordingly, in yet another embodiment, spinal support system 1 includes a helmet support element 20 that mechanically engages with a helmet 22 also worn by the system's wearer, as shown in FIG. 7. The helmet support element 20 may comprise, for example, a support member 20a extending longitudinally from the top vertebral element 32 of SVS 30 substantially parallel to the wearer's cervical vertebrae and terminating in a solid grasping element 20b capable of mechanically engaging with, and supporting, a helmet worn by the wearer. Preferably, helmet grasping element 20b quickly and easily disengages to permit the wearer to remove the helmet. Alternatively, the helmet support member 20 may simply support the weight of the helmet without fixedly gripping. This helmet support member 20 is preferably constructed of a strong yet lightweight polymer such as polyoxymethylene (a.k.a. acetal resin and sold under the brand names such as Delrin® and Celcon) but may also be made of metals such as aluminum alloy or a combination of polymers and metallics. In another preferred embodiment, the helmet support element 20 is integrated directly into the vehicle seat or into a body armor suit worn by the wearer such as the Outer Tactical Vest (OTV) of the Interceptor body armor fielded by the U.S. Army. The helmet support element 20 is designed to physically support the weight of the wearer's helmet such that any forces applied to the head and/or neck of the wearer may also be reduced by the operation of the spinal support system 1.

In addition to the previously described applications, the present invention has several applications in the medical field. For example, the spinal support system could be used in the orthopedic rehabilitation context to help support the spine of a patient who has recently undergone spinal disc replacement surgery or the like. Because of the unique aspects of the present invention, the spinal support system has the ability to tightly control the movement of a wearer's spine, when such control is necessary to prevent movement of, for example, graft material that may have been inserted during lumbar fusion surgery to remedy a spinal disc herniation, while simultaneously allowing freedom of movement to the wearer in other parts of the body and active control of the spinal movement when necessary. Use of the present invention may also help to slow the progression of degenerative diseases such as arthritis or kyphosis, i.e. rounding of the back. Alternately, assisting patients with scoliosis is a logical application. The present spinal support system may be adapted for daily use, by, for example, integrating it into a jacket, shirt, or other item of clothing worn by the user, as described in more detail above.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

What is claimed is:

1. A spinal support system for a seated occupant of a vehicle, comprising:
    an upper body adapter for engaging said seated occupant above the abdomen;
    a structural column engaged at a first end to said upper body adapter, said structural column further comprising,
    a plurality of vertebral elements coupled together and arranged serially end-to-end, and
    a tendon coupling said vertebral elements and configured to affect the alignment of said plurality of vertebral elements;
    a seat support fixture attached to a second end of said structural column, said seat support fixture being configured for attachment to a seat of said vehicle for redirecting loads to said seat rather than said seated occupant's body; and
    an actuator secured relative to said seat support fixture and operatively connected to said tendon for selectively adjusting tension in said tendon, and thereby stiffness of said structural column.

2. The spinal support system of claim 1, additionally comprising a mechanical control element coupled to said tendon and configured to tension/payout/retract said tendon to thereby affect alignment of said plurality of vertebral elements.

3. The spinal support system of claim 1, additionally comprising
    a lower body adapter for engaging said human wearer below the abdomen, said structural column being engaged at said second end to said lower body adapter.

4. The spinal support system of claim 2, wherein said mechanical control element comprises a passive mechanical element chosen from among the group of springs, dampers, and levers.

5. The spinal support system of claim 1, wherein said actuator comprises any one from among the group of electromechanical, pneumatic, hydraulic, electromagnetic, adaptive/smart material actuators.

6. The spinal support system of claim 4, wherein said mechanical control element comprises a spring configured for imparting a pre-bias to said tendon.

7. The spinal support system of claim 5, further comprising at least one sensor.

8. The spinal support system of claim 7 further comprising a programmable controller in communication with said sensor(s) and said actuator, whereby said controller commands said actuator to vary the tension/payout/retraction of said tendon in response to said sensor to reduce loads transmitted to the back of said wearer.

9. The spinal support system of claim 1 configured for redirecting loads applied above the seated occupant's abdomen to the seat of said vehicle.

10. The spinal support system of claim 1, wherein said seat support fixture is permanently attached to said seat.

11. The spinal support system of claim 1, wherein said upper body adapter is adjustable to accommodate varying size human wearers.

12. The spinal support system of claim 3 wherein said upper body adapter, lower body adapter and structural column position the spine of said wearer into a desired position.

13. The spinal support system of claim 12 wherein said desired position increases the effective load bearing capacity of the wearer's spine in a particular loading direction by redirecting said load away from the human wearer's spine in a manner mechanically analogous to a short-circuit.

14. The spinal support system of claim 1 further comprising a helmet support fixture attached to said structural column for redirecting loads from a helmet worn by said human wearer to said vehicle seat.

15. The spinal support system of claim 1, wherein said serial end-to-end arrangement of said plurality of vertebral elements is achieved via intervertebral elements, each of said intervertebral elements forming a single-axis hinge at each end-to-end connection between two of said vertebral elements.

16. The spinal support system of claim 15, wherein at least one of said intervertebral elements forms an effective multi-axis hinge such as that achieved with a spherical bearing between two of said vertebral elements.

17. The spinal support system of claim 1, wherein said plurality of vertebral elements is serially connected in such a way to allow for at least one stably aligned position.

18. The spinal support system of claim 1, wherein said vertebral elements contain physical features that allow for at least one stably aligned position.

19. The spinal support system of claim 1, wherein said tendon is a plurality of tendons, and wherein each of said vertebral elements has a plurality of apertures there though for passing said plurality of tendons.

20. The spinal support system of claim 1, wherein each of said vertebral elements has an aperture there through such that said serial end-to-end arrangement coaxially aligns said aperatures, through which said tendon passes to affect alignment.

21. The spinal support system of claim 20, wherein said aperture through said vertebral elements is non-circular.

22. The spinal support system of claim 3, wherein said lower body adapter is adjustable to accommodate varying size human wearers.

23. A spinal support system for a seated occupant of a vehicle, comprising:
- an upper body adapter for engaging a seated occupant of said vehicle above the abdomen;
- a structural column engaged at a first end to said upper body adapter, said structural column further comprising,
  - a plurality of vertebral elements coupled together and arranged serially end-to-end,
  - a tendon coupling said vertebral elements and configured to affect alignment of said plurality of vertebral elements;
- a seat support fixture attached to a second end of said structural column, said seat support fixture being configured for attachment to a seat of said vehicle for redirecting loads to said seat rather than said seated occupant's body;
- an actuator secured relative to said seat support fixture and operatively coupled to said tendon for imparting tension/payout/retraction to affect the alignment of said plurality of vertebral elements, wherein at least one orientation exists where said plurality of vertebral elements impart a degree of rigidity to said structural column;
- a sensor for measuring tension in said tendon; and
- a programmable controller in communication with said sensor and said actuator for varying tension/payout/retraction of said tendon in response to tension of said sensor to reduce loads transmitted to the back of said seated occupant.

24. The spinal support system of claim 23, further comprising a passive mechanical element chosen from among the group of springs, dampers, and levers operatively coupled to said tendon.

25. The spinal support system of claim 23, wherein said actuator comprises any one chosen from among the group of electromechanical, pneumatic, hydraulic, electromagnetic, adaptive/smart material actuators.

26. The spinal support system of claim 23 further comprising a helmet support fixture attached to said structural column for redirecting loads from a helmet worn by said human wearer to another location.

27. The spinal support system of claim 23, wherein said programmable controller commands said actuator to vary the tension or payout/retraction of said tendon in response to said sensor to provide orthopedic assistance to the back of said wearer.

* * * * *